(12) United States Patent
Hwang et al.

(10) Patent No.: US 10,238,333 B2
(45) Date of Patent: Mar. 26, 2019

(54) DAILY COGNITIVE MONITORING OF EARLY SIGNS OF HEARING LOSS

(71) Applicant: International Business Machines Corporation, Armonk, NY (US)

(72) Inventors: Inseok Hwang, Austin, TX (US); Su Liu, Austin, TX (US); Eric J. Rozner, Austin, TX (US); Chin Ngai Sze, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 88 days.

(21) Appl. No.: 15/236,064

(22) Filed: Aug. 12, 2016

(65) Prior Publication Data

US 2018/0042546 A1    Feb. 15, 2018

(51) Int. Cl.
| | |
|---|---|
| *G06F 17/00* | (2006.01) |
| *A61B 5/00* | (2006.01) |
| *G10L 15/18* | (2013.01) |
| *A61B 5/12* | (2006.01) |
| *A61B 5/16* | (2006.01) |

(Continued)

(52) U.S. Cl.
CPC ............ *A61B 5/4803* (2013.01); *A61B 5/125* (2013.01); *A61B 5/165* (2013.01); *A61B 5/4842* (2013.01); *A61B 5/681* (2013.01); *A61B 5/6898* (2013.01); *A61B 5/7203* (2013.01); *A61B 5/7264* (2013.01); *A61B 5/7275* (2013.01); *G10L 15/18* (2013.01); *G10L 25/51* (2013.01); *A61B 2562/0204* (2013.01); *G10L 25/21* (2013.01)

(58) Field of Classification Search
CPC . H04R 2225/55; H04R 2460/07; H04R 25/50
See application file for complete search history.

(56) References Cited

U.S. PATENT DOCUMENTS

| | | |
|---|---|---|
| 5,428,998 A | 7/1995 | Downs |
| 6,319,207 B1 | 11/2001 | Naidoo |

(Continued)

FOREIGN PATENT DOCUMENTS

CN        201349237 Y        11/2009

OTHER PUBLICATIONS

Anonymous, "System and Method to Calculate Potential Risk of Hearing Loss Using Telephony Devices," IP.com, Prior Art Database Technical Disclosure, Jun. 19, 2014, pp. 1-3.

(Continued)

*Primary Examiner* — Thomas H Maung
(74) *Attorney, Agent, or Firm* — Zilka-Kotab, P.C.

(57) ABSTRACT

In one embodiment, a computer program product includes a computer readable storage medium having program instructions embodied therewith. The embodied program instructions are executable by a processing circuit to cause the processing circuit to receive collected data from one or more data collection devices. The collected data is aggregated over a period of time lasting at least one month, and the collected data includes audio data of a user of the one or more data collection devices. The embodied program instructions also cause the processing circuit to store the audio data to a computer readable storage medium. Moreover, the embodied program instructions cause the processing circuit to analyze the audio data for indications of hearing loss in the user over the period of time.

14 Claims, 7 Drawing Sheets

(51) Int. Cl.
*G10L 25/51* (2013.01)
*G10L 25/21* (2013.01)

(56) References Cited

U.S. PATENT DOCUMENTS

| | | | |
|---|---|---|---|
| 7,258,671 B2 | 8/2007 | Wasden | |
| 2008/0125672 A1 | 5/2008 | Burrows et al. | |
| 2011/0301969 A1 | 12/2011 | Pendse | |
| 2012/0029383 A1 | 2/2012 | Henriksen et al. | |
| 2013/0274628 A1 | 10/2013 | Fausti et al. | |
| 2014/0379352 A1* | 12/2014 | Gondi | G10L 25/63 704/271 |
| 2017/0049368 A1* | 2/2017 | Dillon | A61B 5/123 |
| 2017/0150282 A1* | 5/2017 | Mishra | H04R 5/04 |

OTHER PUBLICATIONS

Anonymous, "Method and Apparatus for Frequency Transposition Mobile for Audio Impaired," IP.com, Prior Art Database Technical Disclosure, Sep. 30, 2015, pp. 1-12.

Rajkumar et al., "Adaptive Expert System for Audiologists," IEEE, 2011, pp. 305-309.

Aldonate et al, "Newborn hearing screener based on automatic auditory brainstem response detection," Biodevices, International Conference on Biomedical Electronics and Devices, 2008, pp. 174-177.

Berry et al., "SenseCam 2010," Proceedings of the 2nd Annual Sensecam Symposium, Sep. 16-17, 2010, pp. 1-74.

Lu et al., "SpeakerSense: Energy Efficient Unobtrusive Speaker Identification on Mobile Phones," Microsoft Research, 2011, pp. 1-18.

Microsoft, "Microsoft Research: SenseCam Overview," Microsoft Corporation, 2013, retrieved from http://research.microsoft.com/en-us/um/cambridge/projects/sensecam/ on Aug. 10, 2016, 1 page.

Lin et al., "Hearing Loss and Incident Dementia," Archives of Neurology, vol. 68, No. 2, Feb. 2011, pp. 214-220.

Asha, "Who Should be Screened for Hearing Loss?" American Speech-Language-Hearing Association, retrieved from http://www.asha.org/public/hearing/Who-Should-be-Screened/ on Aug. 10, 2016, 1 page.

Graham, J., "'Insuficient' Evidence for Routine Hearing Tests, Experts Say," The New York Times, The New Old Age Caring and Coping, Aug. 14, 2012, retrieved from http://newoldage.blogs.nytimes.com/2012/08/14/in-testing-for-hearing-loss-how-often-is-too-often/?_r=1 on Aug. 10, 2016, pp. 1-3.

Asha, "Adult Aural/Audiologic Rehabilitaion," American Speech-Language-Hearing Association, retrieved from http://www.asha.org/public/hearing/Adult-Aural-Rehabilitation/ on Aug. 10, 2016, pp. 1-3.

Lee et al., "SocioPhone: Everyday Face-to-Face Interaction Monitoring Platform Using Multi-Phone Sensor Fusion," ACM, MobiSys '13, Jun. 25-28, 2013, pp. 1-14.

Rachuri et al., "EmotionSense: A Mobile Phones based Adaptive Platform for Experimental Social Psychology Research," ACM, UbiComp '10, Sep. 26-29, 2010, pp. 1-10.

Choudhury, T., "Sensing and Modeling Human Networks using the Sociometer," ISWC, 2003, retrieved from https://www.cs.cornell.edu/~tanzeem/pubs/choudhury_iswc2003.pdf on Aug. 10, 2016, pp. 1-7.

Google, "Hotword Detection, OK Google voice search & actions," Google, 2016, retrieved from https://support.google.com/websearch/answer/2940021?co=GENIE.Plafform%3DAndroid&hl=en on Aug. 10, 2016, pp. 2-3.

Lena Research Foundation, retrieved from https://www.lena.org/about/ on Aug. 10, 2016, pp. 1-12.

Jacobs et al., "Development and Evaluation of a Portable Audiometer for High-Frequency Screening of Hearing Loss From Ototoxicity in Homes/Clinics," IEEE Transactions on Biomedical Engineering, vol. 59, No. 11, Nov. 2012, pp. 3097-3103.

\* cited by examiner

DAILY COGNITIVE MONITORING OF EARLY SIGNS OF HEARING LOSS

BACKGROUND

The present invention relates to detecting early signs of hearing loss, and more specifically, to detecting early signs of hearing loss using long term monitoring of routine interactions and behaviors.

Hearing loss is the third most common health condition affecting older adults, following behind hypertension and arthritis according to the New York Times. Hearing loss affects approximately 30-35% of adults between the ages of 65 and 75 years old. Hearing loss increases as a function of age during the aging process, and is known as presbycusis. Moreover, about 14% of adults between the ages of 45 and 64 have some amount of hearing loss, and about eight million adults between the ages of 18 and 44 have some hearing loss.

Medical guidelines indicate that adults should be screened for hearing loss every ten years through the age of 50, and at three year intervals thereafter. However, many adults do not have regular hearing tests administered. Some barriers to self-awareness or self-acceptance of hearing loss include the chronic nature of the hearing loss process over multiple years, and the hearing loss is too slow to notice. Many adults just assume that everyone else is mumbling. Ignorance or denial are common and the most important barrier to hearing aid use.

Among 2,232 retired older adults surveyed by the American Speech-Language-Hearing Association (ASHA), 76% said that their hearing was of great importance to them; however, fewer than half of the survey participants had undergone a hearing test in the past five years. Nationally, fewer than 15% of seniors aged 65 and older are believed to have regular hearing tests.

Hearing loss also leads to poor cognitive function and aids in the onset of dementia, according to Frank Lin, M D, et al. "Hearing Loss and Incident Dementia," Archives of Neurology, vol. 68, no. 2 (2011). Also, people with hearing problems sometimes try to control conversations by doing most of the talking, while others choose to withdraw from difficult social activities to avoid the strain and fatigue needed to hear. Hearing loss can also lead to feelings of embarrassment and shame and can affect a person's self-esteem.

Once hearing loss is found, attempts may be made to improve day-to-day functioning for the person with hearing loss, but may only be attempted once the hearing loss is detected. Such attempts include controlling the noise in the environment, carrying and using earplugs, keeping audio playback device to no more than half volume (or some other safe listening level that will not damage hearing further), limiting exposure time to loud irritating environments, etc. Moreover, attempts may be made to learn assertive communication, e.g., allow people to get the attention of a person with hearing loss before speaking, learn how and when to ask to rephrase a query, etc., learn how to use visual cues, e.g., read a speaker's facial expression, body language, contextual information, etc., re-arranging everyday spaces, e.g., rearranging furniture to ensure face-to-face view is possible, changing lighting to ensure good lighting on a conversation partner's face, installing carpeting for ambient noise absorption, etc. In addition, hearing assistive technologies, hearing aids, or cochlea implants may be utilized to overcome the hearing loss.

SUMMARY

In one embodiment, a system includes a processing circuit and logic integrated with the processor, executable by the processor, or integrated with and executable by the processor. The logic is configured to cause the processing circuit to receive collected data from one or more data collection devices. The collected data is aggregated over a period of time lasting at least one month, and the collected data includes audio data of a user of the one or more data collection devices. The logic also causes the processing circuit to store the audio data to a computer readable storage medium and analyze the audio data for indications of hearing loss in the user over the period of time.

In another embodiment, a computer program product includes a computer readable storage medium having program instructions embodied therewith. The embodied program instructions are executable by a processing circuit to cause the processing circuit to receive collected data from one or more data collection devices. The collected data is aggregated over a period of time lasting at least one month, and the collected data includes audio data of a user of the one or more data collection devices. The embodied program instructions also cause the processing circuit to store the audio data to a computer readable storage medium and analyze the audio data for indications of hearing loss in the user over the period of time.

In yet another embodiment, a computer-implemented method includes receiving collected data from one or more data collection devices. The collected data is aggregated over a period of time lasting at least one month, and the collected data includes audio data of a user of the one or more data collection devices. The method also includes storing the audio data to a computer readable storage medium and analyzing the audio data for indications of hearing loss in the user over the period of time.

Other aspects and embodiments of the present invention will become apparent from the following detailed description, which, when taken in conjunction with the drawings, illustrate by way of example the principles of the invention.

DETAILED DESCRIPTION

Figure 1:
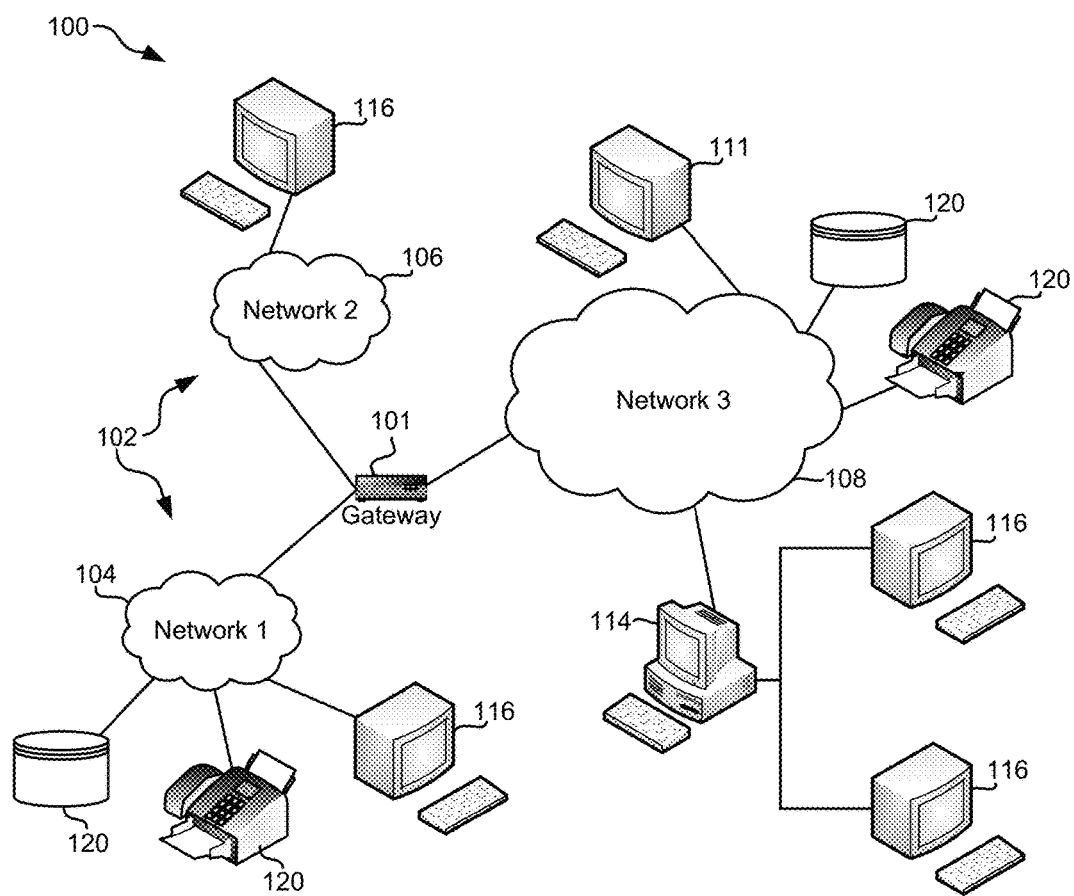
FIG. 1 illustrates a network architecture, in accordance with one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "about" as used herein indicates the value preceded by the term "about," along with any values reasonably close to the value preceded by the term "about," as would be understood by one of skill in the art. When not indicated otherwise, the term "about" denotes the value preceded by the term "about" ±10% of the value. For example, "about 10" indicates all values from and including 9.0 to 11.0.

The following description discloses several preferred embodiments of systems, methods, and computer program products for everyday hearing loss monitoring using data collection and analysis to discover long term trends of hearing loss.

In one general embodiment, a system includes a processing circuit and logic integrated with the processor, executable by the processor, or integrated with and executable by the processor. The logic is configured to cause the processing circuit to receive collected data from one or more data collection devices. The collected data is aggregated over a period of time lasting at least one month, and the collected data includes audio data of a user of the one or more data collection devices. The logic also causes the processing circuit to store the audio data to a computer readable storage medium and analyze the audio data for indications of hearing loss in the user over the period of time.

In another general embodiment, a computer program product includes a computer readable storage medium having program instructions embodied therewith. The embodied program instructions are executable by a processing circuit to cause the processing circuit to receive collected data from one or more data collection devices. The collected data is aggregated over a period of time lasting at least one month, and the collected data includes audio data of a user of the one or more data collection devices. The embodied program instructions also cause the processing circuit to store the audio data to a computer readable storage medium and analyze the audio data for indications of hearing loss in the user over the period of time.

In yet another general embodiment, a computer-implemented method includes receiving collected data from one or more data collection devices. The collected data is aggregated over a period of time lasting at least one month, and the collected data includes audio data of a user of the one or more data collection devices. The method also includes storing the audio data to a computer readable storage medium and analyzing the audio data for indications of hearing loss in the user over the period of time.

FIG. 1 illustrates an architecture 100, in accordance with one embodiment. As shown in FIG. 1, a plurality of remote networks 102 are provided including a first remote network 104 and a second remote network 106. A gateway 101 may be coupled between the remote networks 102 and a proximate network 108. In the context of the present architecture 100, the networks 104, 106 may each take any form including, but not limited to a LAN, a WAN such as the Internet, public switched telephone network (PSTN), internal telephone network, etc.

In use, the gateway 101 serves as an entrance point from the remote networks 102 to the proximate network 108. As such, the gateway 101 may function as a router, which is capable of directing a given packet of data that arrives at the gateway 101, and a switch, which furnishes the actual path in and out of the gateway 101 for a given packet.

Further included is at least one data server 114 coupled to the proximate network 108, and which is accessible from the remote networks 102 via the gateway 101. It should be noted that the data server(s) 114 may include any type of computing device/groupware. Coupled to each data server 114 is a plurality of user devices 116. User devices 116 may also be connected directly through one of the networks 104, 106, 108. Such user devices 116 may include a desktop computer, lap-top computer, hand-held computer, printer or any other type of logic. It should be noted that a user device 111 may also be directly coupled to any of the networks, in one embodiment.

A peripheral 120 or series of peripherals 120, e.g., facsimile machines, printers, networked and/or local storage units or systems, etc., may be coupled to one or more of the networks 104, 106, 108. It should be noted that databases and/or additional components may be utilized with, or integrated into, any type of network element coupled to the networks 104, 106, 108. In the context of the present description, a network element may refer to any component of a network.

According to some approaches, methods and systems described herein may be implemented with and/or on virtual systems and/or systems which emulate one or more other systems, such as a UNIX system which emulates an IBM z/OS environment, a UNIX system which virtually hosts a MICROSOFT WINDOWS environment, a MICROSOFT WINDOWS system which emulates an IBM z/OS environment, etc. This virtualization and/or emulation may be enhanced through the use of VMWARE software, in some embodiments.

In more approaches, one or more networks 104, 106, 108, may represent a cluster of systems commonly referred to as a "cloud." In cloud computing, shared resources, such as processing power, peripherals, software, data, servers, etc., are provided to any system in the cloud in an on-demand relationship, thereby allowing access and distribution of services across many computing systems. Cloud computing typically involves an Internet connection between the systems operating in the cloud, but other techniques of connecting the systems may also be used.

Figure 2:
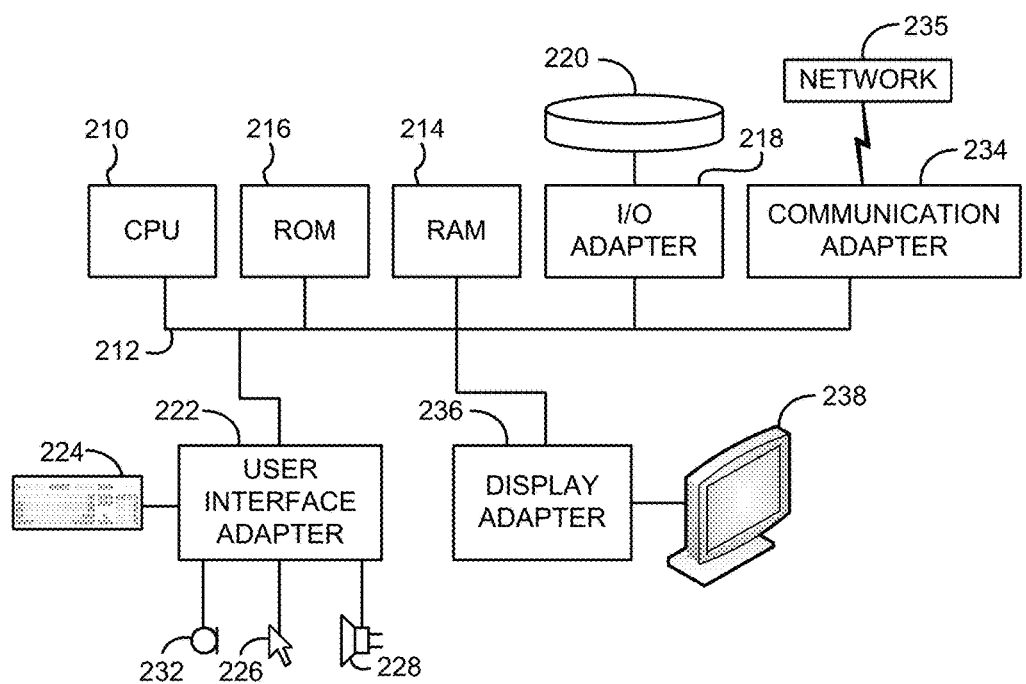
FIG. 2 shows a representative hardware environment that may be associated with the servers and/or clients of FIG. 1, in accordance with one embodiment.

FIG. 2 shows a representative hardware environment associated with a user device 116 and/or server 114 of FIG. 1, in accordance with one embodiment. Such figure illustrates a typical hardware configuration of a workstation having a central processing unit 210, such as a microprocessor, and a number of other units interconnected via a system bus 212.

The workstation shown in FIG. 2 includes a Random Access Memory (RAM) 214, Read Only Memory (ROM) 216, an I/O adapter 218 for connecting peripheral devices such as disk storage units 220 to the bus 212, a user interface adapter 222 for connecting a keyboard 224, a mouse 226, a speaker 228, a microphone 232, and/or other user interface devices such as a touch screen and a digital camera (not shown) to the bus 212, communication adapter 234 for connecting the workstation to a communication network 235

(e.g., a data processing network) and a display adapter 236 for connecting the bus 212 to a display device 238.

The workstation may have resident thereon an operating system such as the Microsoft Windows® Operating System (OS), a MAC OS, a UNIX OS, etc. It will be appreciated that a preferred embodiment may also be implemented on platforms and operating systems other than those mentioned. A preferred embodiment may be written using XML, C, and/or C++ language, or other programming languages, along with an object oriented programming methodology. Object oriented programming (OOP), which has become increasingly used to develop complex applications, may be used.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 3:
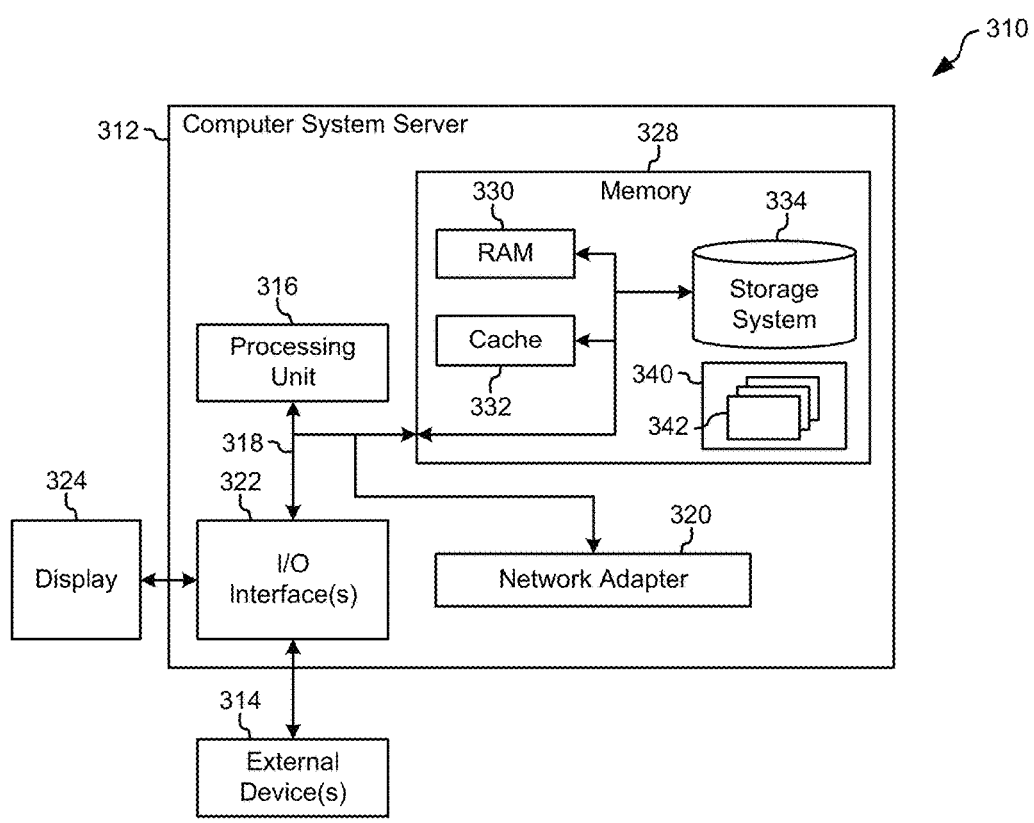
FIG. 3 depicts a cloud computing node according to one embodiment.

Referring now to FIG. 3, a schematic of an example of a cloud computing node is shown. Cloud computing node 310 is only one example of a suitable cloud computing node and is not intended to suggest any limitation as to the scope of use or functionality of embodiments of the invention described herein. Regardless, cloud computing node 310 is capable of being implemented and/or performing any of the functionality set forth hereinabove.

In cloud computing node 310 there is a computer system/server 312, which is operational with numerous other general purpose or special purpose computing system environments or configurations. Examples of well-known computing systems, environments, and/or configurations that may be suitable for use with computer system/server 312 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 312 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 312 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 312 in cloud computing node 310 is shown in the form of a general-purpose computing device. The components of computer system/server 312 may include, but are not limited to, one or more processors or processing units 316, a system memory 328, and a bus 318 that couples various system components including system memory 328 to the one or more processors or processing units 316.

Bus 318 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 312 typically includes a variety of computer system readable media. Such media may be any available media that is accessible by computer system/server 312, and it includes both volatile and non-volatile media, removable and non-removable media.

System memory 328 can include computer system readable media in the form of volatile memory, such as random access memory (RAM) 330 and/or cache memory 332. Computer system/server 312 may further include other removable/non-removable, volatile/non-volatile computer system storage media. By way of example only, storage system 334 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 318 by one or more data media interfaces. As will be further depicted and described below, memory 328 may include at least one program product having a set (e.g., at least one) of program modules that are configured to carry out the functions of embodiments of the invention.

Program/utility 340, having a set (at least one) of program modules 342, may be stored in memory 328 by way of example, and not limitation, as well as an operating system, one or more application programs, other program modules, and program data. Each of the operating system, one or more application programs, other program modules, and program data or some combination thereof, may include an implementation of a networking environment. Program modules 342 generally carry out the functions and/or methodologies of embodiments of the invention as described herein.

Computer system/server 312 may also communicate with one or more external devices 314 such as a keyboard, a pointing device, a display 324, etc.; one or more devices that enable a user to interact with computer system/server 312; and/or any devices (e.g., network card, modem, etc.) that enable computer system/server 312 to communicate with one or more other computing devices. Such communication can occur via Input/Output (I/O) interfaces 322. Still yet, computer system/server 312 can communicate with one or more networks such as a local area network (LAN), a general wide area network (WAN), and/or a public network (e.g., the Internet) via network adapter 320. As depicted, network adapter 320 communicates with the other components of computer system/server 312 via bus 318. It should be understood that although not shown, other hardware and/or software components could be used in conjunction with computer system/server 312. Examples, include, but are not limited to: microcode, device drivers, redundant processing units, external disk drive arrays, RAID systems, tape drives, and data archival storage systems, etc.

Figure 4:
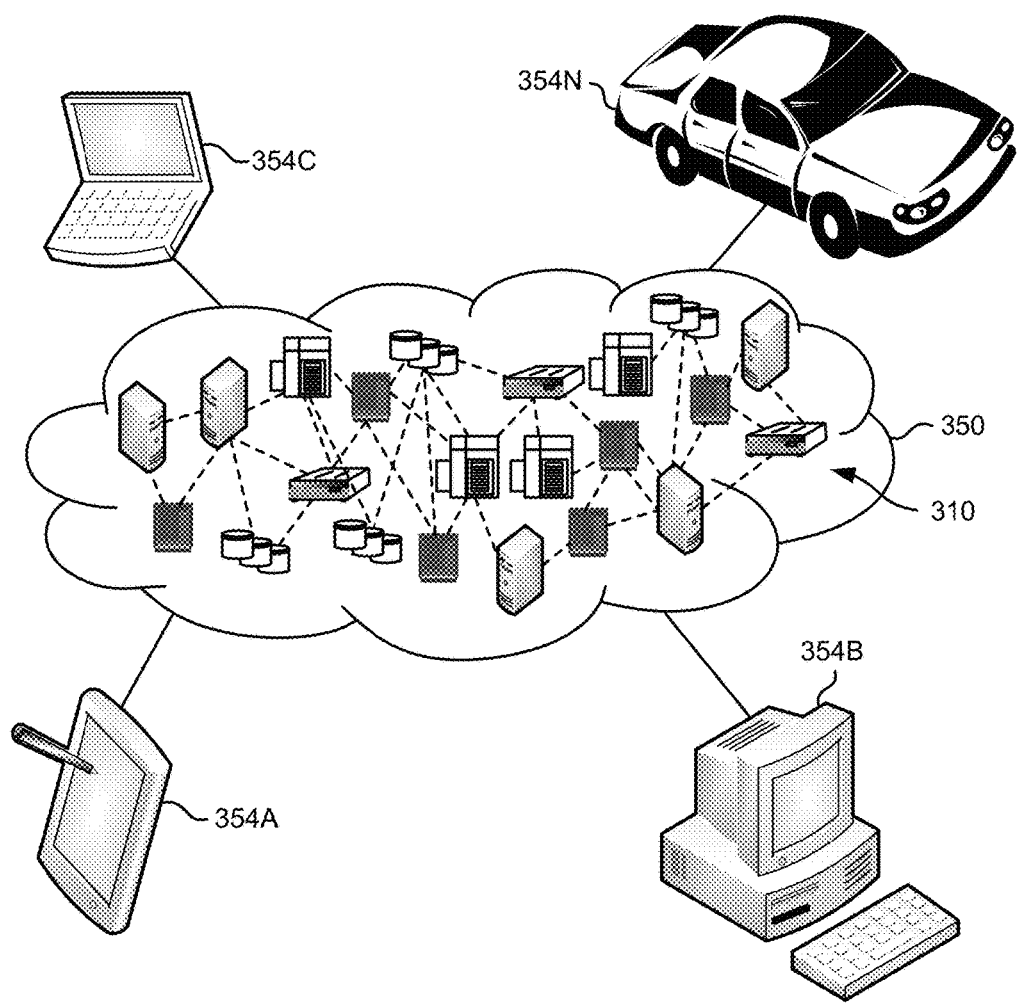
FIG. 4 depicts a cloud computing environment according to one embodiment.

Referring now to FIG. 4, illustrative cloud computing environment 350 is depicted. As shown, cloud computing environment 350 includes one or more cloud computing nodes 310 with which local computing devices used by cloud consumers, such as, for example, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 4 are intended to be illustrative only and that computing nodes 310 and cloud computing environment 350 can communicate with any type of computerized device over any type of network and/or network addressable connection (e.g., using a web browser).

Figure 5:
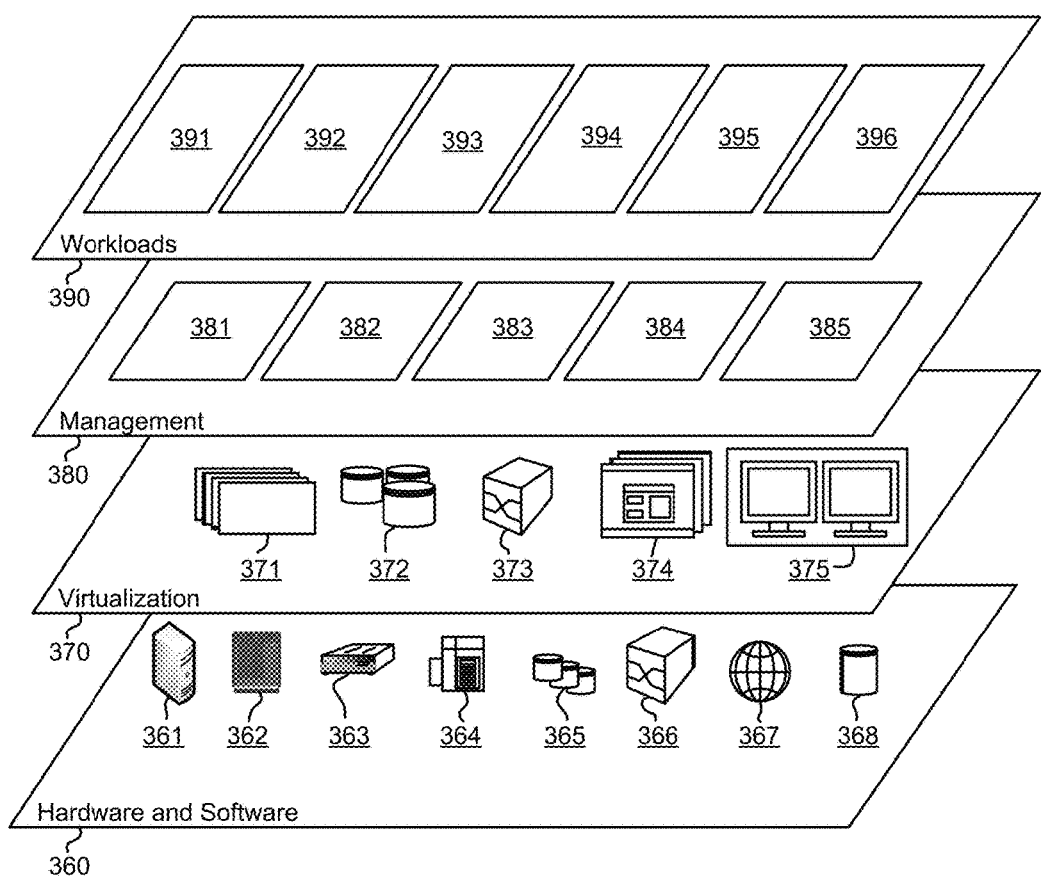
FIG. 5 depicts abstraction model layers according to one embodiment.

Referring now to FIG. 5, a set of functional abstraction layers provided by cloud computing environment 350 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 360 includes hardware and software components. Examples of hardware components include: mainframes 361; RISC (Reduced Instruction Set Computer) architecture based servers 362; servers 363; blade servers 364; storage devices 365; and networks and networking components 366. In some embodiments, software components include network application server software 367 and database software 368.

Virtualization layer 370 provides an abstraction layer from which the following examples of virtual entities may be provided: virtual servers 371; virtual storage 372; virtual networks 373, including virtual private networks; virtual applications and operating systems 374; and virtual clients 375.

In one example, management layer 380 may provide the functions described below. Resource provisioning 381 provides dynamic procurement of computing resources and other resources that are utilized to perform tasks within the cloud computing environment. Metering and Pricing 382 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 383 provides access to the cloud computing environment for consumers and system administrators. Service level management 384 provides cloud computing resource allocation and management such that required service levels are met. Service Level Agreement (SLA) planning and fulfillment 385 provide pre-arrangement for, and procurement of, cloud computing resources for which a future requirement is anticipated in accordance with an SLA.

Workloads layer 390 provides examples of functionality for which the cloud computing environment may be utilized. Examples of workloads and functions which may be provided from this layer include: mapping and navigation 391; software development and lifecycle management 392; virtual classroom education delivery 393; data analytics processing 394; transaction processing 395; and long term hearing loss monitoring and alerting 396.

Because hearing loss is such a common issue with all people as they grow older, and because it is very difficult to be self-aware of one's own gradual hearing loss, which is exacerbated by the low rate of formal hearing tests taken by seniors nationwide (less than 15%), a method for detecting early signs of hearing loss has been designed, according to embodiments described herein, that helps users know themselves earlier with minimal interruption in day-to-day life while still offsetting the seriously harmful effects that hearing loss makes on quality of life.

Figure 6:
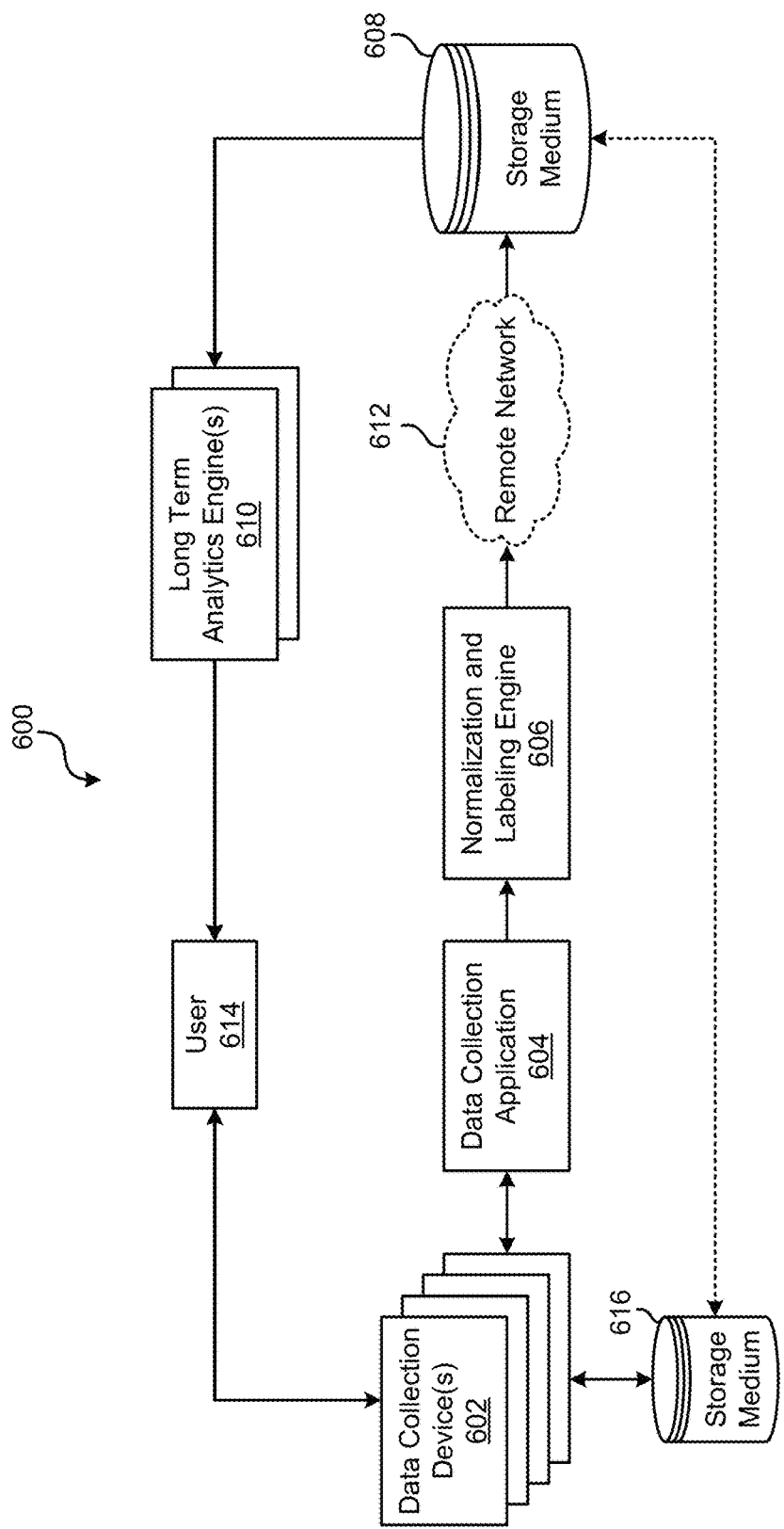
FIG. 6 shows a system according to one embodiment.

Now referring to FIG. 6, a block diagram of a system 600 is shown according to one embodiment. The system 600 may include one or more data collection devices 602, each of which may have operating thereon a data collection application 604, a normalization and labeling engine 606, a computer readable storage medium 608, and at least one long term analytics engine 610.

According to one embodiment, a data collection device 602 may be an easily transportable computer hardware device that is configured to monitor situations of a user 614, such as a conversation between the user 614 and another person, the user 614 making or receiving a telephone call, the user 614 shopping in a supermarket, the user 614 ordering food at a restaurant, playback of recorded audio content listened to by the user 614, or any other situation in which the hearing capability of the user 614 may be monitored.

To this end, in various embodiments, the data collection devices 602 may include a mobile telephone, a smartwatch, a tablet, a digital wearable assistant, a portable audio playback device, etc.

In one embodiment, a mobile telephone may be any smartphone or cellular telephone known in the art that includes a microprocessor and is configured to execute logic, such as an APPLE iPHONE handset, a GOOGLE NEXUS handset, a SAMSUNG GALAXY handset, etc.

In another embodiment, a portable audio playback device may be any portable playback device known in the art that includes a microprocessor and is configured to execute logic to playback recorded content and/or accessible content wirelessly, such as an APPLE iPOD, a SONY WALKMAN MP3 player, a SANDISK Flash MP3 player, etc.

In accordance with another embodiment, a tablet may be any personal computer or computing device that is in the form of a tablet, slate, or convertible laptop known in the art that has a flat screen and microprocessor and is configured to execute logic, such as an APPLE iPAD, a SAMSUNG GALAXY TAB, a MCIROSOFT SURFACE, an HP TOUCHPAD, etc.

According to another embodiment, a smartwatch may be any wrist wearable computing device known in the art that includes a processor therein for executing logic, and in some embodiments may be configured to wirelessly connect to a smartphone. Examples of smartwatches include an APPLE WATCH, a SAMSUNG GEAR, a SONY SMARTWATCH, an ASUS ZENWATCH, etc.

In yet another embodiment, a digital wearable assistant may be any electronic device that includes a hardware processor that is configured to execute logic to collect relevant data from situations in which the user 614 exhibits hearing capability. For example, a digital wearable assistant may include a microprocessor, a computer readable storage medium, a microphone, and a power supply. The microprocessor may be affixed to a button or broach and may be electrically connected to the power supply, the computer readable storage medium, and the microphone to enable the microprocessor to collect and store interactions made by the user in various situations that exhibit the user's hearing capability at any given time. Then, the microprocessor may provide this collected data to the data collection application 604, which may be operating on a home computer, smartphone, or some other device regularly visited by the user 614. One example of a digital wearable assistant is a sociometer, as described in T. Choudhury & A. Pentland, "Sensing and modeling human networks using the Sociometer," ISWC 2013.

According to more embodiments, a data collection device 602 may be a device that resides in a location normally frequented by the user 614, such as the user's home, place of business, doctor's office, vehicle, etc. In these embodiments, the data collection device 602 may be a laptop computer, a television such as a smart TV configured to collect audio input, a surveillance system or IP camera(s), a web camera, a smart home assistant such as AMAZON ECHO, a smart home hub, an Internet of Things (IOT) processor located within a smart device, a computer running ALEXA software, etc.

It is preferable for the one or more data collection devices 602 to be located and/or transportable with the user 614 to as many locations that the user 614 frequents as possible to provide the most data collection opportunities available. In this way, with more and more audio input collected over time, smaller trends of hearing loss are able to be detected quicker and with more accuracy, thereby allowing the hearing loss problem to be addressed sooner.

The collected data may be provided to the data collection application 604 wirelessly, such as via Bluetooth, radio frequency, near field communication (NFC), wireless local area connection (WLAN), etc., or via a hardwire connection, such as universal serial bus (USB), Ethernet, a specialized cradle, etc.

The collected data may be sorted as audio data and metadata stored as a tuple having two or more values associated together, e.g., {value1, value2}. The values may be selected to provide context to the audio data included in the collected data, such as an ID of the speaker (user), a speaking volume in which a conversation was held, another party's speaking volume during the conversation with the user, a listening volume of playback device during music listening or some other listening activity, a timestamp in which the data was recorded, etc.

In another embodiment, the collected data may include a tally of the number of times that the user 614 requested or queried for a term or phrase (e.g., spoken dialog) to be repeated, tallied over a period of time. As the user 614 requests to repeat things more frequently, e.g., more often per time period, it is determined that hearing loss is occurring. This type of data may also be collected and stored to be used to determine a user's hearing loss over a long period of time.

In one embodiment, the data collection application 604 and/or logic may store the collected data in a local computer readable storage medium 616 that is local to the one or more data collection devices 602, such as RAM, ROM, non-volatile memory (NVM) like Flash, a removable memory card like a SECURE DIGITAL (SD) or COMPACTFLASH, a hard disk operated by a hard disk drive (HDD), a solid state device (SSD), etc.

Moreover, in another embodiment, the data collection application 604 and/or logic may store the collected data in a remote storage medium 608 that is located remotely from the one or more data collection devices 602, and may be accessible in some embodiments via a remote network 612, such as cloud storage, or some other remotely accessible storage medium known in the art.

In a further embodiment, the data collection application 604, normalization and labeling engine 606, computer readable storage medium 608, and at least one long term analytics engine 610 may all be located remotely from the user 614 and the at least one data collection device 602 and accessible via the remote network 612, such as via residing in the cloud, utilizing distributed computing, and/or other techniques known in the art for removing processing and storage demands from local devices and executing such functionality remotely.

In another embodiment, the collected data may be synchronized between a local storage medium 616 and a remote storage medium 608, and/or the remote storage medium 608 may be updated with new data periodically from the local storage medium 616, thereby reducing the size of the local storage medium 616 necessary to store the collected data, that may become large over extended periods of time.

The normalization and labeling engine 606 may be any computing device or logic that is configured to take the collected data as input, analysis the collected data to recognize different inputs (different conversations, start and stop of hearing sessions, times when the user 614 is listening to music, etc.), differentiate between types of input (e.g., audio input such as voice input from the user 614, voice input from other actors, non-voice input such as music, noises, animals, etc.), determine audio data relevant to the user 614 (audio data that provides insight into the user's hearing ability at a particular point in time), detect ambient noise affecting the audio data, detect background noise affecting the audio data, and determine metadata about the user 614 of the one or more data collection devices 602, e.g., the user's identity (name, ID number associated with the user 614, etc.), audio input timestamp, audio input duration, a transcription of the audio data (audio data transcribed into textual data), a user's emotion during production of the audio input, an environment of the situation in which the audio data was recorded, etc.

The identity of a speaker as the user 614 may be determined from the audio input based on voice input from the user 614 that is recorded as a baseline for comparison to audio input obtained from the one or more data collection devices 602. Moreover, in some approaches, the user 614 may initiate a function or routine of the one or more data collection devices 602 that enables the voice input to be detected, possibly by using a hot key press (e.g., pressing a microphone button on a keyboard of a smartphone), speaking a hot word (e.g., saying "OK Google" on a device using the ANDROID operating system), initiating a talk-to-text feature of the one or more data collection devices 602, etc.

The user's emotion impacts the volume level of the user's speech, and therefore may be taken into consideration when determining whether the user 614 is speaking with an elevated voice due to hearing loss, or due to the emotion in the situation, e.g., the user's elevated speaking voice may be discounted when it is determined that the user 614 is speaking emotionally. Emotion may be inferred from a user's speech based on recognizable patterns of elevated speech, cracking voice, emphasis on words and parts of words, etc., that are indicators of emotion being present and are not utilized during normal speaking.

Moreover, background noise and ambient noise may cause the user 614 to raise the speaking voice to be heard over the other noise, and therefore may also be taken into consideration when determining whether the user 614 is suffering from or exhibiting factors of hearing loss, e.g., the user's elevated speaking voice may be discounted when ambient and/or background noise is elevated similarly.

In one embodiment, the normalization and labeling engine 606 may be configured to normalize all audio data with ambient noise level to provide a consistent set of data from which hearing loss trends may be determined over long periods of time. For the sake of these descriptions, long periods of time include time frames of longer than one month, more preferably longer than one year, and most preferably over the course of several years or even decades. Techniques for detecting hearing loss which are applied at singular time frames, such as hearing tests, are useful for routine check-ups, but are not capable of providing the daily cognitive analysis which the techniques described herein according to various embodiments enables and provides.

Moreover, in one embodiment, the normalization and labeling engine 606 may be configured to label the audio data with the metadata prior to storing the audio data to the storage medium 608. In this way, the user 614 may be identified from the audio data, along with a time of recording for the audio data. In this way, the at least one long term analytics engine 610 is able to analyze data from more than one user without the various sources of data being mixed up.

The at least one long term analytics engine 610 may include any computing device configured to perform analysis on the audio data stored to the storage medium 608 using any known analysis techniques available, such as regression analysis, inferential analysis, predictive analysis, casual analysis, trend estimation, mechanistic or deterministic analysis, etc. Moreover, once analysis has been performed on the audio data stored to the storage medium 608, the at least one long term analytics engine 610 may be configured to alert the user 614 in response to hearing loss being detected that exceeds a set threshold or percentage of baseline hearing established when the monitoring is started.

Indications of hearing loss include, but are not limited to, elevated speaking or speech volume during conversations or phone calls, elevated listening volumes of audio playback devices, increased frequency of queries to repeat dialog, terms, or phrases, etc.

It is anticipated that routine hearing tests will still be undertaken by the user 614 even when utilizing the data collection and analysis techniques described herein in various embodiments. Moreover, results from the at least one long term analytics engine 610 may be provided to the user

614 periodically, in response to hearing loss that exceeds the set threshold or percentage, and/or on demand in response to input of the user 614, a request from a doctor, audiology consultant, etc.

To allow for outside intervention, the results of the at least one long term analytics engine 610 may be provided to a doctor, audiology consultant, etc., in order for that medical professional to examine the hearing trends and suggest intervention and/or further examination of the user 614.

In one embodiment, an amount (quantitative) of hearing loss may be reported to the user 614 and/or other medical professionals, which may be associated with a time frame of the loss, e.g., a hearing loss of 2.0 decibels has been detected over the last 6 months. In a further embodiment, confidence scores may be calculated along with the results of the at least one long term analytics engine 610 in order to provide a context for how likely it is that hearing loss has actually occurred for any given user. These confidence scores may be calculated using any known confidence analysis techniques, and may be presented as a percentage or some other understandable scheme, e.g., 65% likely that hearing loss of 3.5 decibels has occurred over the last 18 months. In yet another embodiment, a message may be included in the alert to promote action on the part of the user 614, e.g., it is likely (>50%) that hearing loss has occurred—please take corrective actions to lessen additional hearing loss.

Figure 7:
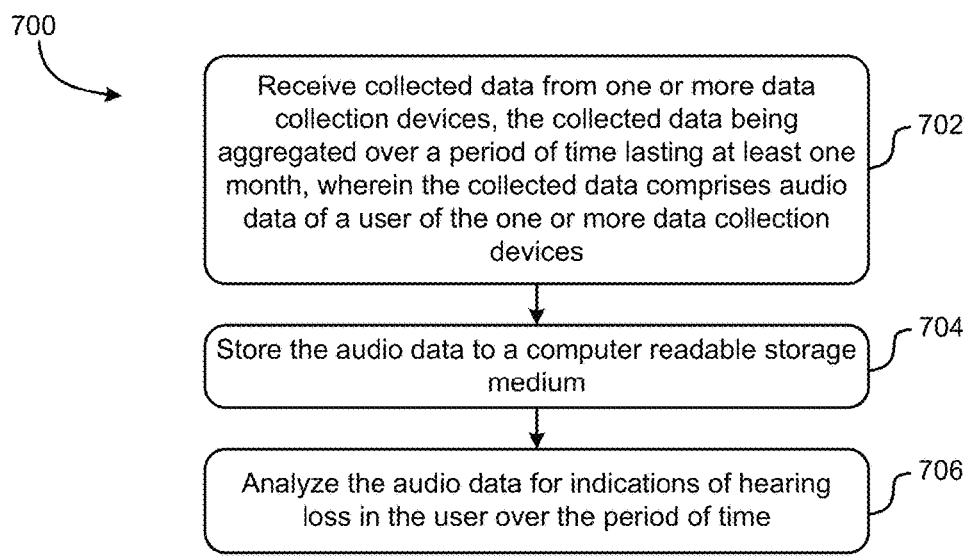
FIG. 7 shows a flowchart of a method, according to one embodiment.

Now referring to FIG. 7, a method 700 is shown according to one embodiment. The method 700 may be performed in accordance with the present invention in any of the environments depicted in FIGS. 1-6, among others, in various embodiments. Of course, more or less operations than those specifically described in FIG. 7 may be included in method 700, as would be understood by one of skill in the art upon reading the present descriptions.

Each of the steps of the method 700 may be performed by any suitable component of the operating environment. For example, in various embodiments, the method 700 may be partially or entirely performed by a cloud server, a mainframe computer, a host, a processing circuit having one or more processors therein, or some other device having one or more processors therein. The processing circuit, e.g., processor(s), chip(s), and/or module(s) implemented in hardware and/or software, and preferably having at least one hardware component, may be utilized in any device to perform one or more steps of the method 700. Illustrative processors include, but are not limited to, a CPU, an ASIC, a FPGA, etc., combinations thereof, or any other suitable computing device known in the art.

As shown in FIG. 7, method 700 may start with optional operation 702, where collected data is received from one or more data collection devices. The collected data has been aggregated over a period of time lasting at least one month, and the collected data includes audio data of a user of the one or more data collection devices. Moreover, in one embodiment, a data collection application may receive the collected data, with the data collection application being executed locally on one or more of the data collection devices, and/or remotely on a server, such as in a cloud-based system.

According to one embodiment, the audio data may include any of the following, among other types of audio data: a conversation in which the user participated, a telephone call received or initiated by the user, and/or playback of recorded audio content listened to by the user.

In another embodiment, the one or more data collection devices may include any of the following types of devices: a mobile telephone, a smartwatch, a tablet, a digital wearable assistant, and/or a portable audio playback device.

In operation 704, the audio data is stored to a computer readable storage medium for later use in analysis for indications of hearing loss.

In one embodiment, the computer readable storage medium may be located remotely from the one or more data collection devices, such as in a cloud-based system. Furthermore, the analysis may also be performed using a processing circuit located remotely from the one or more data collection devices.

In a further embodiment, method 700 may include determining metadata about the audio data, and storing the metadata with the audio data as a tuple having two or more values. The metadata may include an identification of the user and a timestamp for the audio data. In a further embodiment, the metadata may include any of the following: a speaking volume of the user during a conversation, a second speaking volume of another party the conversation with the user, a listening volume of a playback device during audio content playback, and/or a tally of a number of times that the user requested for spoken dialog to be repeated.

In operation 706, the audio data is analyzed for indications of hearing loss in the user over the period of time. In one embodiment, regression analysis may be performed on the audio data to determine indications of hearing loss in the user over the period of time.

In one embodiment, method 700 may further include alerting the user of hearing loss being detected (such as by a message on a smartphone, an email sent to an email address of the user, an automated phone call, etc.) in response to hearing loss that exceeds a set threshold being detected. For example, the threshold may be 90% of a baseline hearing ability measured during a routine hearing test, established with data collected during a first period of time less than the time period over which the data is collected for indications of hearing loss, etc.

In one embodiment, method 700 may include identifying background noise and/or ambient noise from the audio data. This background noise and/or ambient noise may cause elevated speaking volume levels for the user in certain situations. Therefore, method 700 may also include normalizing the audio data to account for the background noise and/or ambient noise prior to storing the audio data.

According to another embodiment, method 700 may include determining whether an emotion of the user caused elevated speech volume in the audio data. This emotion may cause elevated speaking volume levels for the user in certain situations. For example, when a person is mad, happy, excited, etc., the person may talk louder and more forcibly in an attempt to express this emotion, get a point across in an argument, emphasize portions of dialog, etc. Therefore, method 700 may also include normalizing the audio data to account for the emotion of the user prior to storing the audio data.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Moreover, a system according to various embodiments may include a processor and logic integrated with and/or executable by the processor, the logic being configured to perform one or more of the process steps recited herein. By integrated with, what is meant is that the processor has logic embedded therewith as hardware logic, such as an application specific integrated circuit (ASIC), a FPGA, etc. By executable by the processor, what is meant is that the logic is hardware logic; software logic such as firmware, part of an operating system, part of an application program; etc., or some combination of hardware and software logic that is accessible by the processor and configured to cause the processor to perform some functionality upon execution by the processor. Software logic may be stored on local and/or remote memory of any memory type, as known in the art. Any processor known in the art may be used, such as a software processor module and/or a hardware processor such as an ASIC, a FPGA, a central processing unit (CPU), an integrated circuit (IC), a graphics processing unit (GPU), etc.

It will be clear that the various features of the foregoing systems and/or methodologies may be combined in any way, creating a plurality of combinations from the descriptions presented above.

It will be further appreciated that embodiments of the present invention may be provided in the form of a service deployed on behalf of a customer to offer service on demand.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A system, comprising:
a processing circuit and logic integrated with the processing circuit, executable by the processing circuit, or integrated with and executable by the processing circuit, the logic being configured to cause the processing circuit to:
obtain baseline hearing ability for a user;
receive collected data from one or more data collection devices after obtaining the baseline hearing, the collected data being aggregated over a period of time lasting at least one month, wherein the collected data comprises audio data of the user of the one or more data collection devices;
analyze the audio data for indications of hearing loss in the user over the period of time, wherein the logic configured to cause the processing circuit to analyze the audio data comprises logic configured to cause the processing circuit to:
determine whether an emotion of the user and/or at least one noise caused an elevated speech volume, wherein the emotion is determined based on a trait not utilized during normal speaking, and wherein the trait is selected from the group consisting of: a cracking voice of the user, an emphasis on words that indicate the emotion, an emphasis on words that indicate the emotion, an emphasis on parts of words that indicate the emotion, and combinations thereof;
identify the at least one noise from the audio data, the at least one noise being selected from the group consisting of: background noise, ambient noise, and combinations thereof; and
normalize the audio data to account for the emotion of the user and the identified at least one noise, and discount the elevated speech volume accordingly, prior to storing the audio data to a computer readable storage medium; and
analyze the stored audio data for one or more indicia of hearing loss; and
alert the user of the one or more indicia of hearing loss being detected in response to determining hearing loss that exceeds a predetermined threshold percentage of the baseline hearing.

2. The system as recited in claim 1, wherein the logic is further configured to cause the processing circuit to:
determine metadata about the audio data, the metadata comprising at least an identification of the user and a timestamp for the audio data; and
store the metadata with the audio data as a tuple having two or more values.

3. The system as recited in claim 2, wherein the metadata further comprises a tally of a number of times that the user requested for spoken dialog to be repeated over a plurality of periods of time, and wherein an increasing tally of the number of times that the user requested for spoken dialog to be repeated over several time periods is indicative of hearing loss occurring; and
wherein the logic is further configured to cause the processing circuit to quantify an amount of the hearing loss experienced by the user over a predetermined amount of time.

4. The system as recited in claim 1, wherein the audio data is selected from the group consisting of: a conversation in which the user participated, a telephone call received or initiated by the user, playback of recorded audio content listened to by the user, and combinations thereof.

5. The system as recited in claim 1, wherein the one or more data collection devices are selected from the group consisting of: a mobile telephone, a smartwatch, a tablet, a digital wearable assistant, a portable audio playback device, and combinations thereof.

6. The system as recited in claim 1, wherein the threshold percentage is about 90% of the baseline hearing ability of the user.

7. The system as recited in claim 1, wherein the logic is further configured to cause the processing circuit to:
determine metadata about the audio data, the metadata comprising at least an identification of the user and a timestamp for the audio data;
store the metadata with the audio data as a tuple having two or more values, wherein the metadata further comprises a tally of a number of times that the user requested for spoken dialog to be repeated over a plurality of periods of time, and wherein an increasing tally of the number of times that the user requested for spoken dialog to be repeated over several time periods is indicative of hearing loss occurring;
perform regression analysis on the audio data to determine indications of hearing loss in the user over the period of time;
wherein the audio data is selected from the group consisting of: a conversation in which the user participated, a telephone call received or initiated by the user, playback of recorded audio content listened to by the user, and combinations thereof;
wherein the one or more data collection devices are selected from the group consisting of: a mobile telephone, a smartwatch, a tablet, a digital wearable assistant, a portable audio playback device, and combinations thereof; and
wherein the computer readable storage medium is located remotely from the one or more data collection devices.

8. A computer program product, the computer program product comprising a computer readable storage medium having program instructions embodied therewith, the embodied program instructions being executable by a processing circuit to cause the processing circuit to:
obtain, by the processing circuit, baseline hearing for a user;
receive, by the processing circuit, collected data from one or more data collection devices after obtaining the baseline hearing, the collected data being aggregated over a period of time lasting at least one month, wherein the collected data comprises audio data of the user of the one or more data collection devices;
analyze, by the processing circuit, the audio data for indications of hearing loss in the user over the period of time, wherein the program instructions configured to cause the processing circuit to analyze the audio data comprises program instructions configured to cause the processing circuit to:
  determine, using the processing circuit, whether an emotion of the user and/or at least one noise caused an elevated speech volume, wherein the emotion is determined based on a trait not utilized during normal speaking, and wherein the trait is selected from the group consisting of: a cracking voice of the user, an emphasis on words that indicate the emotion, an emphasis on words that indicate the emotion, an emphasis on parts of words that indicate the emotion, and combinations thereof;
  identify, using the processing circuit, the at least one noise from the audio data, the at least one noise being selected from the group consisting of: background noise, ambient noise, and combinations thereof; and
  normalize, using the processing circuit, the audio data to account for the emotion of the user and the identified at least one noise, and discount the elevated speech volume accordingly, prior to storing the audio data to the computer readable storage medium; and
analyze, using the processing circuit, the stored audio data for one or more indicia of hearing loss; and
alert, by the processing circuit, the user of the one or more indicia of hearing loss being detected in response to determining hearing loss that exceeds a predetermined threshold percentage of the baseline hearing being detected as a result of analyzing the audio data.

9. The computer program product as recited in claim 8, wherein the embodied program instructions are further executable by the processing circuit to cause the processing circuit to:
  determine, by the processing circuit, metadata about the audio data; and
  store, by the processing circuit, the metadata with the audio data as a tuple having two or more values,
  wherein the metadata comprises an identification of the user, a timestamp for the audio data, a speaking volume of the user during a conversation, and a tally of a number of times that the user requested for spoken dialog to be repeated over a plurality of periods of time, and wherein an increasing tally of the number of times that the user requested for spoken dialog to be repeated over several time periods is indicative of hearing loss occurring.

10. The computer program product as recited in claim 8, wherein the audio data is selected from the group consisting of: a conversation in which the user participated, a telephone call received or initiated by the user, playback of recorded audio content listened to by the user, and combinations thereof;
  wherein the computer readable storage medium is located remotely from the one or more data collection devices; and
  wherein the one or more data collection devices are selected from the group consisting of: a mobile telephone, a smartwatch, a tablet, a digital wearable assistant, a portable audio playback device, and combinations thereof.

11. The computer program product as recited in claim 8, wherein the embodied program instructions executable to cause the processing circuit to:
  analyze, by the processing circuit, the audio data for indications of hearing loss in the user over the period of time further causes the processing circuit to perform regression analysis on the audio data to determine indications of hearing loss in the user over the period of time; and
  quantify, by the processing circuit, an amount of the hearing loss experienced by the user over a predetermined amount of time.

12. A computer-implemented method, the method comprising:
  obtaining baseline hearing ability for a user;
  receiving collected data from one or more data collection devices after obtaining the baseline hearing, the collected data being aggregated over a period of time lasting at least one month, wherein the collected data comprises audio data of the user of the one or more data collection devices;
  analyzing the audio data for indications of hearing loss in the user over the period of time, wherein analyzing the audio data comprises:
    determining whether an emotion of the user and/or at least one noise caused an elevated speech volume, wherein the emotion is determined based on a trait not utilized during normal speaking, and wherein the trait is selected from the group consisting of: a cracking voice of the user, an emphasis on words that indicate the emotion, an emphasis on words that indicate the emotion, an emphasis on parts of words that indicate the emotion, and combinations thereof;
    identifying the at least one noise from the audio data, the at least one noise being selected from the group consisting of: background noise, ambient noise, and combinations thereof; and
    normalizing the audio data to account for the emotion of the user and the identified at least one noise, and discount the elevated speech volume accordingly, prior to storing the audio data to a computer readable storage medium; and
  analyzing the stored audio data for one or more indicia of hearing loss; and
  alerting the user of hearing loss being detected in response to hearing loss that exceeds a predetermined threshold percentage of the baseline hearing ability being detected as a result of analyzing the audio data.

13. The method as recited in claim 12, further comprising:
  determining metadata about the audio data; and
  storing the metadata with the audio data as a tuple having two or more values,
  wherein the metadata comprises information selected from the group consisting of: an identification of the user, a timestamp for the audio data, a speaking volume of the user during a conversation, and a tally of a number of times that the user requested for spoken dialog to be repeated over a plurality of periods of time, and wherein an increasing tally of the number of times that the user requested for spoken dialog to be repeated over several time periods is indicative of hearing loss occurring.

14. The method as recited in claim 12, wherein the audio data is selected from the group consisting of: a conversation in which the user participated, a telephone call received or initiated by the user, playback of recorded audio content listened to by the user, and combinations thereof;
  wherein the computer readable storage medium is located remotely from the one or more data collection devices; and
  wherein the one or more data collection devices are selected from the group consisting of: a mobile telephone, a smartwatch, a tablet, a digital wearable assistant, a portable audio playback device.

\* \* \* \* \*